United States Patent
Morita et al.

(10) Patent No.: US 6,881,418 B2
(45) Date of Patent: Apr. 19, 2005

(54) LIQUID DEODORANT KILLING MICROORGANISM AND METHOD OF MICROORGANISM-KILLING DEODORIZATION

(75) Inventors: Masahiro Morita, Shizuoka (JP); Masanori Komatsu, Shizuoka (JP); Katsuhisa Isogai, Shizuoka (JP)

(73) Assignee: K.I Chemical Industry Co., Ltd., Iwata-gun (JP)

(*) Notice: Subject to any disclaimer, the term of this patent is extended or adjusted under 35 U.S.C. 154(b) by 0 days.

(21) Appl. No.: 10/343,749

(22) PCT Filed: Jun. 6, 2002

(86) PCT No.: PCT/JP02/05593
§ 371 (c)(1),
(2), (4) Date: Feb. 6, 2003

(87) PCT Pub. No.: WO02/100174
PCT Pub. Date: Dec. 19, 2002

(65) Prior Publication Data
US 2003/0157051 A1 Aug. 21, 2003

(30) Foreign Application Priority Data
Jun. 8, 2001 (JP) ........................................ 2001-174176

(51) Int. Cl.⁷ .............................................. A01N 25/00
(52) U.S. Cl. ...................... 424/405; 424/76.8; 514/389; 514/423
(58) Field of Search ............................... 424/405, 76.8; 514/389, 425, 446, 422, 438, 444, 423, 424, 385

(56) References Cited

U.S. PATENT DOCUMENTS 3,547,887 A * 12/1970 Gabler et al. ................. 528/86
4,119,535 A * 10/1978 White et al. .................. 210/62

FOREIGN PATENT DOCUMENTS

| EP | 232737 | 8/1987 |
| JP | 56-158333 | * 12/1981 |
| JP | 6-080518 | 3/1994 |
| JP | 9-151101 | 6/1997 |
| JP | 11047755 | * 2/1999 |
| JP | 2002-275008 | 9/2002 |
| WO | 00/18689 | 4/2000 |

* cited by examiner

*Primary Examiner*—Neil S. Levy
(74) *Attorney, Agent, or Firm*—Oblon, Spivak, McClelland, Maier & Neustadt, P.C.

(57) ABSTRACT

The object of the present invention is to provide a microbicidal deodorant in a tractable liquid form that has excellent long-term storage stability.

The microbicidal deodorant of the present invention comprises: at least one substance selected from the group consisting of halogenated dialkyl hydantoins represented by the general formula (1) and halogenated succinimides represented by general formula (2); and at least one substance selected from the group consisting of tetrahydrothiophene 1,1-dioxide, 3-methyltetrahydrothiophene 1,1-dioxide, and 2,5-dihydrothiophene 1,1-dioxide.

18 Claims, No Drawings

LIQUID DEODORANT KILLING MICROORGANISM AND METHOD OF MICROORGANISM-KILLING DEODORIZATION

TECHNICAL FIELD

The present invention relates to a microbicidal liquid deodorant, a deodorizing method for killing microbes using the same, and a method for stabilizing a microbicidal liquid deodorant. More specifically, the present invention relates to a novel microbicidal liquid agent containing a halogenated dialkyl hydantoin and a halogenated succinimide which are stabilized by thiophene derivatives such as tetrahydrothiophene-1,1-dioxide and a method for killing microbes using the above, a liquid deodorant and a deodorizing method using the same, and a method for stabilizing these agents.

BACKGROUND ART

In recent years, there have many instances of trouble occurring due to the presence of slime in various types of service water traceable to microbial contamination, and adverse effects have been caused in various fields. Here, the term "slime" means a sticky aggregated or muddy substance which comprises as major components high molecular polysaccharides secreted mainly by microbes, and various types of substance suspended in the water which become incorporated therein. For example, when slime occurs in heat exchangers or pipes of a cooling water system at a chemical factory or the like, cooling efficiency is decreased and sometimes pipes are clogged. Further, when slime forms on the wall surfaces of pipes used in the paper manufacturing process at a paper factory, the slime is flaked off and mixed in white water (back water). Then, spots or coloring are formed on the paper product and deteriorate its quality. This partially decreases paper strength and thus causes paper breakages, forcing the interruption of continuous operations. Therefore, the control of the causative microbes is an important issue.

Further, active sludge at sewage treatment plants, unpleasant odors from wastes or residues, and foul odors from raw garbage at waste treatment plants cause not only on-site working environments to be poor, but also deteriorate the environments of surrounding areas by diffusing such odors to these areas. Thus, prompt odor elimination or deodorization by preventing the occurrence of or by the decomposition of causative agents is essential. However, in the case of existing deodorants, the decomposition or volatilization of their chemical components having deodorant effects results in deterioration of their deodorant effects, and the problem thus exists that the sustainability of their effects is low.

Conventionally, chlorine gas, sodium hypochlorite or potassium hypochlorite solution, or chlorinated isocyanuric acid in tablet or powder form has been used in order to prevent trouble caused by such microbes. However, chlorine gas has disadvantages in that it involves very high risk in the case of leakage, and it is difficult to handle. Further, hypochlorous agents are also disadvantageous in that they do not act effectively on microbes since they do not have permeability into slime. These agents have further disadvantages such as deactivation by organic matters in water, and thus sufficient efficacy cannot be expected.

On the other hand, it is known that halogenated dialkyl hydantoins or halogenated succinimides have microbicidal activities (Zn. Mikrobiol., Epidemiol. Immunobiol. vol.14, No.9, p14–18, 1967, JP Patent Publication (Examined Application) No. 46-27270). However, these compounds are commercially distributed in a solid form such as tablet, powder, or granule, and they are used in the solid form in the field. Therefore, when using these compounds, problems arise in handling safety, that is, the risk of effects on humans such as skin disorders and mucosal inflammation caused by dusting during operation. Further, workability problems are presented, such as the inability to transfer these compounds by pump.

Further, from a microbicidal efficacy aspect, these compounds have sluggish solubility and permeability into target systems. Thus, in order to obtain a sufficient effect in a short period, these compounds must be added in a large amount. In particular, when these compounds are used for water systems with low recirculation rates, for example, cooling water for certain industrial uses or water for paper manufacturing processes, water in the systems is discharged out of the systems before the inputted compounds are completely dissolved. In contrast, when these compounds are used for water systems with high recirculation rates, for example, cooling water for air-conditioning, the sluggish rate of dissolution of the inputted compounds increases the probability of the growth of resistant microbes in the system. Also, due to the sluggish rate of dissolution and sluggish permeability of these compounds, prompt deodorizing effects after their input cannot be obtained. Therefore, in the case of using these compounds as deodorants, the addition of large amounts thereof is required, resulting in cost increase.

Most solid compounds having microbicidal activity are used as liquid agent by dissolving them into, in general, glycols, glycol ethers, aprotic polar solvents or water, or mixture solvents of these with water. This allows easy handling of microbicidal solid compounds. Liquidizing microbicidal solid compounds in this manner provides these compounds with excellent workability at the time of use, and at the same time, also provides them with other advantages such as quick dissolution and permeation of active ingredients into target systems to be treated for microbes or deodorization. Namely, in comparison with the case where solid compounds are inputted into the target systems as solid agents, adding smaller amounts of these compounds within a shorter period enables killing of microbes and deodorization in the target systems. Therefore, liquidizing microbicidal solid compounds is an extremely effective means for cost reduction.

However, when halogenated dialkyl hydantoins and halogenated succinimides are prepared as liquid agents with generally used organic solvents, a large volume of irritant corrosive gas is immediately generated. Further, in this case, microbicidal active ingredients are deactivated within a very short period, and thus the compounds can no longer be used as microbicidal and deodorizing agents. In other words, liquid agents containing halogenated dialkyl hydantoins and halogenated succinimides have disadvantages such as corrosive gas generation and poor stability. Furthermore, with regard to liquid compositions containing derivatives of halogenated dialkyl hydantoins, a method using water and cyclic amide compounds including ε-caprolactam and succinimide has been already suggested (JP Patent Publication (Examined Application) No. 56-37961). Although these liquid compositions are better in terms of stability in comparison with liquid compositions prepared using common organic solvents, they do not have sufficient stability as a formulation.

Under these circumstances, there is a need for halogenated dialkyl hydantoin compositions and halogenated succinimide compositions which are liquid for tractability and have excellent stability, i.e. stable in long-term storage. However, a formulated liquid agent suitable for practical use has not been found before.

DISCLOSURE OF INVENTION

In order to solve the above problems, it is an object of the present invention to provide a liquid microbicidal deodorant which comprises a halogenated dialkyl hydantoin and/or a halogenated succinimide as an active ingredient and has excellent workability, safety, stability, and solubility, and a method for killing microbes and deodorizing.

The present inventors have carried out intensive research on the above object. As a result, they have succeeded in formulating a liquid agent in which an effective active ingredient is maintained over a long period but which does not generate any irritant and corrosive gas by using at least one substance selected from the group consisting of tetrahydrothiophene 1,1-dioxide, 3-methyltetrahydrothiophene 1,1-dioxide, and 2,5-dihydrothiophene 1,1-dioxide as a primary solvent. Thus, according to the present invention, there is provided a liquid microbicide and a liquid deodorant which comprise a halogenated dialkyl hydantoin and/or halogenated succinimide in a stable state, and a method for killing microbes and a method for deodorizing using these. Namely, the present invention includes the following:

(1) A liquid microbicide comprising: at least one substance selected from the group consisting of halogenated dialkyl hydantoins represented by the following general formula (1):

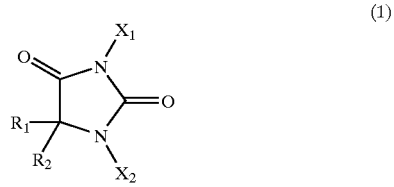

(1)

wherein $X_1$ and $X_2$ represent halogen atoms and $R_1$ and $R_2$ represent low alkyl groups, and
halogenated succinimides represented by the following general formula (2):

(2)

wherein Y represents a halogen atom; and
at least one substance selected from the group consisting of tetrahydrothiophene 1,1-dioxide, 3-methyltetrahydrothiophene 1,1-dioxide, and 2,5-dihydrothiophene 1,1-dioxide.

(2) The liquid microbicide described in (1) above, wherein the halogenated dialkyl hydantoin is 1,3-dibromo-5,5-dimethylhydantoin, 1-bromo-3-chloro-5,5-dimethylhydantoin, 3-bromo-1-chloro-5,5-dimethylhydantoin, bromochloro-5,5-dimethylhydantoin, 1,3-dichloro-5,5-dimethylhydantoin, or 1,3-dichloro-5-ethyl-5-methylhydantoin.

(3) The liquid microbicide described in (1) above, wherein the halogenated succinimide is N-chlorosuccinimide or N-bromosuccinimide.

(4) The liquid microbicide described in (1) above, comprising a halogenated dialkyl hydantoin and tetrahydrothiophene 1,1-dioxide.

(5) The liquid microbicide described in any one of (1) to (4) above, further comprising at least one substance selected from the group consisting of hydantoin, 5,5-dimethylhydantoin, succinimide, and phthalimide.

(6) The liquid microbicide described in any one of (1) to (5) above, further comprising a known microbicide component.

(7) A method for killing microbes, comprising the step of treating a target system or a target object for microbicidal treatment with the liquid microbicide described in any one of (1) to (6) above.

(8) A liquid deodorant comprising at least one substance selected from the group consisting of halogenated dialkyl hydantoins represented by the above general formula (1) and halogenated succinimides represented by the above general formula (2), and at least one substance selected from the group consisting of tetrahydrothiophene 1,1-dioxide, 3-methyltetrahydrothiophene 1,1-dioxide, and 2,5-dihydrothiophene 1,1-dioxide.

(9) The liquid deodorant described in (8) above, wherein the halogenated dialkyl hydantoin is 1,3-dibromo-5,5-dimethylhydantoin, 1-bromo-3-chloro-5,5-dimethylhydantoin, 3-bromo-1-chloro-5,5-dimethylhydantoin, bromochloro-5,5-dimethylhydantoin, 1,3-dichloro-5,5-dimethylhydantoin, or 1,3-dichloro-5-ethyl-5-methylhydantoin.

(10) The liquid deodorant described in (8) above, wherein the halogenated succinimide is N-chlorosuccinimide or N-bromosuccinimide.

(11) The liquid deodorant described in (8) above, comprising a halogenated dialkyl hydantoin and tetrahydrothiophene 1,1-dioxide.

(12) The liquid deodorant described in any one of (8) to (11) above, further comprising at least one substance selected from the group consisting of hydantoin, 5,5-dimethylhydantoin, succinimide, and phthalimide.

(13) The liquid deodorant described in any one of (8) to (12) above, further comprising a known microbicide component.

(14) A deodorizing method comprising the step of treating a target object or a target system for deodorization with the liquid deodorant described in any one of (8) to (13) above.

(15) A method for stabilizing a halogenated dialkyl hydantoin and/or halogenated succinimide, comprising the step of: dissolving at least one substance selected from the group consisting of halogenated dialkyl hydantoins represented by the above general formula (1) and halogenated succinimides represented by the above general formula (2), in at least one substance selected from the group consisting of tetrahydrothiophene 1,1-dioxide, 3-methyltetrahydrothiophene 1,1-dioxide, and 2,5-dihydrothiophene 1,1-dioxide.

(16) The method for stabilizing a halogenated dialkyl hydantoin and/or halogenated succinimide described in (15) above, wherein at least one substance selected from the group consisting of hydantoin, 5,5-dimethylhydantoin, succinimide, and phthalimide is dissolved.

The halogenated dialkyl hydantoin to be used for the liquid microbicide and liquid deodorant (hereinafter referred to as microbicidal liquid deodorant) of the present invention is represented by the above general formula (1). In the general formula (1), examples of halogen represented by $X^1$ and $X^2$ include bromide and chlorine. Here, $X^1$ and $X^2$ may be the same or different. Further, examples of lower alkyl groups represented by $R^1$ and $R^2$ include alkyl groups having a carbon number from 1 to 3, such as methyl groups, ethyl groups, and propyl groups, and preferably alkyl groups having a carbon number from 1 to 2. Here, $R^1$ and $R^2$ may be the same or different. These halogenated dialkyl hydantoins can be produced by first obtaining dialkyl hydantoin from a dialkyl ketone, a cyanide, or a carbonate, and halogenating dialkyl hydantoin.

Specific compounds of the halogenated dialkyl hydantoin are exemplified as follows.
Compound A1: 1,3-dibromo-5,5-dimethylhydantoin
Compound A2: 1-bromo-3-chloro-5,5-dimethylhydantoin
Compound A3: 3-bromo-1-chloro-5,5-dimethylhydantoin
Compound A4: bromochloro-5,5-dimethylhydantoin
Compound A5: 1,3-dichloro-5,5-dimethylhydantoin
Compound A6: 1,3,-dichloro-5-ethyl-5-methylhydantoin These halogenated dialkyl hydantoins may be used either alone or in combination of two or more. Among these compounds, the selection for use is preferably carried out from the group consisting of compounds A1 to A4.

Halogenated dialkyl hydantoins are commercially available, and these may be used. Examples of commercially available halogenated dialkyl hydantoin include HALO-COM DBH (High Polymer Labs, the above-described Compound A1), AQUABROM (Great Lakes Chemical Corporation, the above-described Compound A2), and DANTOBROM RW (Lonza, a mixture of the above-described Compounds A4, A5, and A6).

Further, the halogenated succinimide to be used for the microbicidal liquid deodorant is represented by the above general formula (2). In the general formula (2), examples of halogen represented by Y include bromide and chlorine. These halogenated succinimides are produced by halogenating succinimide using a halogenating agent such as metal hypochlorite or hypochlorite.

Specific compounds of halogenated succinimides are exemplified as follows.
Compound B1: N-bromosuccinimide
Compound B2: N-chlorosuccinimide The halogenated succinimides may be used either alone or in combination of two or more. Further, the halogenated dialkyl hydantoin and halogenated succinimide may be used in combination for the microbicidal liquid deodorant of the present invention.

Thiophene derivatives to be used as a primary solvent for the microbicidal liquid deodorant of the present invention are exemplified as follows.
Compound C1: tetrahydrothiophene 1,1-dioxide
Compound C2: 3-methyltetrahydrothiophene 1,1-dioxide
Compound C3: 2,5-dihydrothiophene 1,1-dioxide These thiophene derivatives may be used either alone or in combination of two or more. Namely, at least one compound selected from the group consisting of Compounds C1 to C3 is used as a primary solvent for the microbicidal liquid deodorant of the present invention.

The microbicidal liquid deodorant of the present invention is prepared by mixing and stirring at least one substance selected from the group consisting of halogenated dialkyl hydantoins (general formula (1)) and halogenated succinimides (general formula (2)), and at least one of the above thiophene derivatives. In some cases, the mixing and stirring are preferably conducted while heating at 40 to 50° C. for 10 minutes to approximately 1 hour.

Further, an adjuvant or the like is preferably added to the microbicidal liquid deodorant. Examples of the adjuvant include at least one substance selected from the group consisting of hydantoin, 5,5-dimethylhydantoin, succinimide, and phthalimide. The solubility of halogenated dialkyl hydantoin and/or halogenated succinimide can be further enhanced by inclusion of the adjuvant in the microbicidal liquid deodorant. As long as the adjuvant is a compound selected from the group mentioned above, these may be used either alone or in combination of two or more.

The above-mentioned primary solvent is preferably mixed in an amount of 100 or more parts by mass, more preferably 200 to 900 parts by mass, based on 100 parts by mass of halogenated dialkyl hydantoin and/or halogenated succinimide. Employing the above range of the mixing amount of the primary solvent can enhance the stability of the microbicidal liquid deodorant.

In addition, the adjuvant is preferably mixed in an amount of 1 to 50 parts by weight, more preferably 5 to 20 parts by weight, based on 100 parts by mass of halogenated dialkyl hydantoin and/or halogenated succinimide.

Furthermore, the microbicidal liquid deodorant of the present invention may be mixed with a generally used inexpensive organic solvent and/or water at the time of formulation or practical use.

Examples of usable organic solvents include: glycols such as ethylene glycol, diethylene glycol, dipropylene glycol, and polyethylene glycol; glycol ethers such as ethyl cellosolve, methyl carbitol, and dipropylene glycol monomethyl ether; esters such as propylene carbonate, 4-butyrolactone, dimethyl glutarate, dimethyl adipate, dimethyl succinate, and dimethyl maleate; amides such as N-methylacetamide, acetamide, 2-pyrrolidinone, and ε-caprolactam; and alcohols such as isopropyl alcohol and octanol. Among these, it is particularly preferable to use propylene carbonate, 4-butyrolactone, 2-pyrrolidinone, and N-methylacetamide. These organic solvents may be used either alone or in combination of two or more.

The microbicidal liquid deodorant of the present invention may be diluted with these organic solvents and/or water at an arbitrary dilution ratio. The mixing ratio of organic solvent and/or water is preferably 1 to 99% by mass, more preferably 10 to 90% by mass, and most preferably 30 to 70% by mass.

The microbicidal liquid deodorant of the present invention may be used for the purpose of killing microbes, deodorizing, or both of these. The targets for application of the microbicidal liquid deodorant, that is systems or objects to be treated for killing microbes and deodorizing, are not particularly limited, and various applications are possible. The microbicidal liquid deodorant of the present invention can exhibit microbicidal and/or deodorant effects more quickly than the conventional solid type. As target objects for application of the microbicidal liquid deodorant, paper manufacturing processes, cooling or washing water for industrial use, cooling water for air-conditioning, industrial water, pools, baths, activated sludge wastes or residues, and raw garbage are exemplified. When the microbicidal liquid deodorant is used for paper manufacturing processes, cooling or washing water for industrial use, cooling water for air-conditioning, industrial water, pools, baths, etc., disinfection and bacteriostasis can be effectively accomplished and slime formation can also be inhibited. Further, when the microbicidal liquid deodorant is used for activated sludge wastes or residues, raw garbage, etc., deodorization can effectively be accomplished.

A proper input amount of the microbicidal liquid deodorant differs and is appropriately determined depending on the pH of the target object or system, the contents of organic or inorganic matters, the odor intensity, or the like. Generally, the input amount is determined such that halogenated dialkyl hydantoin and/or halogenated succinimide are present in a concentration of 0.1 to 1000 ppm, preferably 5 to 100 ppm. Inputting an amount of the microbicidal liquid deodorant within the above range produces sufficient microbicidal and/or deodorant effects as well as concurrent economical advantages.

Combining the microbicidal liquid deodorant of the present invention with known microbicide components enables the enlargement of the antibacterial spectrum, and the obtainment of additional or synergistic effects of the antibacterial ability. Examples of known microbicide components include bromonitro compounds such as 2,2-dibromo-2-nitroethanol, 2,2-dibromo-2-nitroethyl=formate, 2,2-dibromo-2-nitroethyl=acetate, 2,2-dibromo-2-nitroethyl=propanoate, 2-bromo-2-nitropropane-1,3-diol, 2-bromo-2-nitropropan-1,3-diyl=diorama, and 2-bromo-2-nitropropane-1,3-diyl=diacetate (hereinafter referred to as "BNDA"), methylenbisthiocyanate, 3,3,4,4-tetrachlorotetrahydrothiophene-1,1-dioxide, 5-chloro-2,4,6-trifluoroisophthalonitrile, 1-bromomethyl-2-bromo-1,2-ethanedinitrile, di-n-decyl dimethyl ammonium chloride, and benzalkonium chloride. Among these, 2,2-dibromo-2-nitroethanol or 2-bromo-2-nitropropane-1,3-diyl=acetate is preferably mixed.

Target microbes to be treated with the microbicidal liquid deodorant of the present invention may include bacterium, eumycetes such as yeasts and filamentous fungus, and algae. Examples of bacterium include: gram negative bacterium such as *Escherichia* genus, *Pseudomonas* genus, *Vibrio* genus, *Enterobacter* genus, *Serratia* genus, *Legionella* genus, and *Salmonella* genus; and gram positive bacterium such as *Staphylococcus* genus, *Bacillus* genus, *Streptococcus* genus, and *Lactobacillus* genus. Examples of yeasts include *Saccharomyces* genus, *Candida* genus, *Geotrichum* genus, *Hansenula* genus, *Rhodotrula* genus, *Kluyveromyces* genus, and *Pichia* genus. Examples of filamentous fungus include *Aspergillus* genus, *Penicillium* genus, *Trichoderma* genus, *Mucor* genus, *Rhizopus* genus, *Fusarium* genus, *Cladosporium* genus, and *Alternaria* genus. Examples of algae include *Chlorella* genus, *Oscillatoria* genus, *Anabaena* genus, *Senedesmus* genus, and *Clostetium* genus.

INDUSTRIAL APPLICABILITY

The microbicidal liquid deodorant of the present invention can maintain halogenated dialkyl hydantoin and/or halogenated succinimide, which have been difficult to liquidize in a stable condition, in a stable condition over a long-term. Therefore, according to the present invention, there is provided a microbicidal liquid deodorant which can be preserved without change of properties as a liquid agent for a long term. Further, since the microbicidal liquid deodorant of the present invention is a liquid agent, it can exhibit prompt microbicidal and/or deodorant effects, which are not observed in the case of solid agents. Thus, the present invention provides a microbicidal liquid deodorant which has excellent safety and workability and is free from dusting, a drawback of the solid agents.

BEST MODE FOR CARRYING OUT THE INVENTION

The present invention will hereinafter be described in detail with reference to Examples, Comparative Examples and Test Examples, but the technical scope of the present invention is not limited thereto. Examples were obtained by mixing with each component and stirring with heat at 45° C. for 15 minutes. The mixture of compounds A4, A5, and A6 used in the tests was prepared by mixing the compounds at a ratio of 60, 30, and 10 parts by weight, respectively.

TABLE 1

| Formulation | | Composition (% by mass) |
|---|---|---|
| Example 1 | Compound A1 | 12.0 |
| | Compound C1 | 88.0 |
| Example 2 | Compound A2 | 30.0 |
| | Compound C1 | 66.0 |
| | 5,5-dimethylhydantoin | 4.0 |
| Example 3 | Mixture of Compound A4, A5, and A6 (6:3:1) | 18.0 |
| | Compound C1 | 50.0 |
| | 4-butyrolactone | 32.0 |
| Example 4 | Compound B1 | 15.0 |
| | Compound C1 | 85.0 |
| Example 5 | Compound B2 | 10.0 |
| | Compound C1 | 40.0 |
| | propylene carbonate | 50.0 |
| Example 6 | Compound A1 | 12.0 |
| | Compound C2 | 88.0 |
| Example 7 | Compound A2 | 12.0 |
| | Compound C1 | 88.0 |
| Example 8 | Compound A1 | 20.0 |
| | Compound C1 | 77.5 |
| | hydatoin | 2.5 |
| Example 9 | Compound A2 | 42.0 |
| | Compound C1 | 53.0 |
| | hydatoin | 5.0 |
| Example 10 | Compound A2 | 25.0 |
| | Compound C1 | 46.5 |
| | Compound C2 | 25.0 |
| | succinimide | 3.5 |
| Example 11 | Mixture of Compound A4, A5, and A6 (6:3:1) | 15.0 |
| | Compound C1 | 80.0 |
| | Compound C3 | 5.0 |
| Example 12 | Compound B1 | 20.0 |
| | Compound C2 | 78.0 |
| | phtahlimide | 2.0 |
| Example 13 | Compound A1 | 15.0 |
| | Compound C1 | 70.0 |
| | BNDA | 15.0 |
| Comparative Example 1 | Compound A1 | 12.0 |
| | N,N-dimethylacetamide | 88.0 |
| Comparative Example 2 | Compound A2 | 20.0 |
| | ϵ-caprolactam | 45.0 |
| | water | 35.0 |
| Comparative Example 3 | Compound A2 | 10.0 |
| | N-methyl-2-pyrrolidinone | 90.0 |
| Comparative Example 4 | Compound B1 | 10.0 |
| | 4-butyrolactone | 90.0 |
| Comparative Example 5 | Compound B2 | 10.0 |
| | 4-butyrolactone | 90.0 |

TEST EXAMPLE 1

Stability Test

Twenty-ml graduated test tubes were filled respectively with each compound having the formulation shown in Table 1, and each of the test tubes was sealed so as to leave no bubbles with a silicone stopper having a U-shaped glass tube, one side of which was attached to penetrate the silicone stopper for discharging generated gas. Each whole device was placed gently inside a glass beaker and the opening of the beaker was covered with aluminum foil. The beaker was allowed to stand in an incubator at 40° C. for a predetermined number of days. The volume of gas generated with the lapse of time was measured by reading the graduation, and corrosion of the aluminum foil caused by the generated gas was observed. The results are shown in Tables 2 and 3.

Tables 2 and 3 indicate the respective results obtained by conducting the tests over two separate occasions under the above conditions.

TABLE 2

| | | Lapse of days | | | |
|---|---|---|---|---|---|
| | | 3 days | 7 days | 14 days | 28 days |
| Example 1 | Volume of generated gas (ml) | 0 | 0 | 0 | 0 |
| | Presence of corrosion | none | none | none | none |
| Example 2 | Volume of generated gas (ml) | 0 | 0 | 0 | 0.0 |
| | Presence of corrosion | none | none | none | none |
| Example 3 | Volume of generated gas (ml) | 0 | 0 | 0 | 0 |
| | Presence of corrosion | none | none | none | none |
| Example 4 | Volume of generated gas (ml) | 0 | 0 | 0 | 0.2 |
| | Presence of corrosion | none | none | none | none |
| Example 5 | Volume of generated gas (ml) | 0 | 0 | 0 | 0 |
| | Presence of corrosion | none | none | none | none |
| Comparative Example 1 | Volume of generated gas (ml) | 0.4 | 2.0 | 4.5 | 7.0 |
| | Presence of corrosion | none | present | present | present |
| Comparative Example 2 | Volume of generated gas (ml) | 0 | 0.3 | 1.1 | 2.6 |
| | Presence of corrosion | none | none | present | present |
| Comparative Example 3 | Volume of generated gas (ml) | 0.2 | 1.8 | 5.0 | 6.5 |
| | Presence of corrosion | present | present | present | present |
| Comparative Example 4 | Volume of generated gas (ml) | 0.2 | 1.7 | 3.0 | 4.5 |
| | Presence of corrosion | present | present | present | present |

TABLE 3

| | | Lapse of days | | | |
|---|---|---|---|---|---|
| | | 3 days | 7 days | 14 days | 28 days |
| Example 8 | Volume of generated gas (ml) | 0 | 0 | 0 | 0 |
| | Presence of corrosion | none | none | none | none |
| Example 9 | Volume of generated gas (ml) | 0 | 0 | 0 | 0 |
| | Presence of corrosion | none | none | none | none |
| Example 10 | Volume of generated gas (ml) | 0 | 0 | 0 | 0 |
| | Presence of corrosion | none | none | none | none |
| Example 11 | Volume of generated gas (ml) | 0 | 0 | 0 | 0.2 |
| | Presence of corrosion | none | none | none | none |
| Example 12 | Volume of generated gas (ml) | 0 | 0 | 0 | 0 |
| | Presence of corrosion | none | none | none | none |
| Comparative Example 1 | Volume of generated gas (ml) | 0.6 | 2.5 | 4.0 | 6.0 |
| | Presence of corrosion | none | present | present | present |
| Comparative Example 2 | Volume of generated gas (ml) | 0 | 0.5 | 1.6 | 3.0 |
| | Presence of corrosion | none | present | present | present |
| Comparative Example 3 | Volume of generated gas (ml) | 0.5 | 1.8 | 4.0 | 6.0 |
| | Presence of corrosion | present | present | present | present |
| Comparative Example 5 | Volume of generated gas (ml) | 0.2 | 0.4 | 2.5 | 4.0 |
| | Presence of corrosion | present | present | present | present |

The results of Tables 2 and 3 show that the Examples generated an extremely smaller volume of gas compared with the Comparative Examples and did not cause corrosiveness. Thus, it was found that the Examples are safe and stable microbicidal liquid deodorants.

TEST EXAMPLE 2

Confirmation Test for Stability of Microbicidal Effects

Each compound having the formulation of Table 1 was poured into a glass bottle, and each glass bottle was sealed hermetically, and allowed to stand in an incubator at 50° C. for 4 weeks. The compounds of these bottles were compared with the just-prepared unheated liquid agents in terms of microbicidal activity. *Escherichia* genus microbes, which were subjected to cell washing, were added to phosphate/citrate buffer solution (pH 8) to a concentration of approximately $10^6$ CFU/ml, and each liquid agent was then added thereto so as to have a prescribed concentration (indicated based on active ingredient) and the mixture was shaken for 1 hour in an L shape tube. Thereafter, each mixture was diluted with sterilized water, inoculated onto a nutrient plate agar medium, and cultured in an incubator for 3 days at 30° C. Then, viable cells therein were counted. The results are shown in Tables 4 and 5 in the unit of CFU/ml. Tables 4 and 5 indicate the respective results obtained by conducting the tests over two separate occasions under the above conditions.

TABLE 4

| | Conc. (ppm) | Heating (50° C., 4 weeks) | No heating (Immediately after preparation) |
|---|---|---|---|
| Example 1 | 0.96 | $<10^2$ | $<10^2$ |
| | 0.72 | $<10^2$ | $<10^2$ |
| | 0.48 | $2.0 \times 10^2$ | $<10^2$ |
| | 0.24 | $5.1 \times 10^6$ | $7.1 \times 10^5$ |
| Example 2 | 1.8 | $<10^2$ | $<10^2$ |
| | 1.2 | $<10^2$ | $<10^2$ |
| | 0.6 | $<10^2$ | $<10^2$ |
| | 0.3 | $4.8 \times 10^5$ | $6.9 \times 10^5$ |
| Example 4 | 1.2 | $<10^2$ | $<10^2$ |
| | 0.9 | $<10^2$ | $<10^2$ |
| | 0.6 | $<10^2$ | $<10^2$ |
| | 0.3 | $6.0 \times 10^4$ | $4.0 \times 10^4$ |
| Example 5 | 0.8 | $<10^2$ | $<10^2$ |
| | 0.6 | $<10^2$ | $<10^2$ |
| | 0.4 | $1.0 \times 10^3$ | $8.0 \times 10^2$ |
| | 0.2 | $1.1 \times 10^5$ | $4.0 \times 10^5$ |

TABLE 4-continued

| | Conc. (ppm) | Heating (50° C., 4 weeks) | No heating (Immediately after preparation) |
|---|---|---|---|
| Comparative Example 1 | 3.84 | $7.0 \times 10^6$ | $<10^2$ |
| | 1.92 | $4.9 \times 10^6$ | $<10^2$ |
| | 0.96 | $5.4 \times 10^6$ | $2.0 \times 10^2$ |
| | 0.48 | $5.5 \times 10^6$ | $7.0 \times 10^3$ |
| Comparative Example 2 | 6.4 | $3.9 \times 10^6$ | $<10^2$ |
| | 3.2 | $3.8 \times 10^6$ | $<10^2$ |
| | 1.6 | $6.3 \times 10^6$ | $<10^2$ |
| | 0.8 | $5.2 \times 10^6$ | $6.0 \times 10^2$ |
| Comparative Example 4 | 3.2 | $3.0 \times 10^6$ | $<10^2$ |
| | 1.6 | $3.8 \times 10^6$ | $<10^2$ |
| | 0.8 | $4.8 \times 10^6$ | $2.0 \times 10^2$ |
| | 0.4 | $5.0 \times 10^6$ | $1.7 \times 10^3$ |
| No treatment | — | $6.0 \times 10^6$ | $6.0 \times 10^6$ |

TABLE 5

| | Conc. (ppm) | Heating (50° C., 4 weeks) | No heating (Immediately after preparation) |
|---|---|---|---|
| Example 6 | 2.0 | $<10^2$ | $<10^2$ |
| | 1.0 | $<10^2$ | $<10^2$ |
| | 0.5 | $<10^2$ | $<10^2$ |
| | 0.25 | $4.0 \times 10^6$ | $9.5 \times 10^5$ |
| Example 7 | 2.0 | $<10^2$ | $<10^2$ |
| | 1.0 | $<10^2$ | $<10^2$ |
| | 0.5 | $<10^2$ | $<10^2$ |
| | 0.25 | $5.2 \times 10^6$ | $1.0 \times 10^6$ |
| Example 8 | 2.0 | $<10^2$ | $<10^2$ |
| | 1.0 | $<10^2$ | $<10^2$ |
| | 0.5 | $<10^2$ | $<10^2$ |
| | 0.25 | $3.8 \times 10^6$ | $5.8 \times 10^5$ |
| Example 10 | 2.0 | $<10^2$ | $<10^2$ |
| | 1.0 | $<10^2$ | $<10^2$ |
| | 0.5 | $<10^2$ | $<10^2$ |
| | 0.25 | $7.6 \times 10^5$ | $4.2 \times 10^5$ |
| Example 11 | 2.0 | $<10^2$ | $<10^2$ |
| | 1.0 | $<10^2$ | $<10^2$ |
| | 0.5 | $<10^2$ | $<10^2$ |
| | 0.25 | $4.2 \times 10^6$ | $5.0 \times 10^6$ |
| Example 12 | 2.0 | $<10^2$ | $<10^2$ |
| | 1.0 | $<10^2$ | $<10^2$ |
| | 0.5 | $<10^2$ | $<10^2$ |
| | 0.25 | $4.7 \times 10^6$ | $5.5 \times 10^6$ |
| Comparative Example 1 | 4.0 | $4.5 \times 10^6$ | $<10^2$ |
| | 2.0 | $4.9 \times 10^6$ | $<10^2$ |
| | 1.0 | $5.0 \times 10^6$ | $<10^2$ |
| | 0.5 | $5.8 \times 10^6$ | $1.0 \times 10^3$ |
| Comparative Example 2 | 4.0 | $3.0 \times 10^6$ | $<10^2$ |
| | 2.0 | $3.8 \times 10^6$ | $<10^2$ |
| | 1.0 | $5.3 \times 10^6$ | $<10^2$ |
| | 0.5 | $5.5 \times 10^6$ | $3.0 \times 10^2$ |
| Comparative Example 5 | 4.0 | $3.3 \times 10^6$ | $<10^2$ |
| | 2.0 | $3.8 \times 10^6$ | $<10^2$ |
| | 1.0 | $4.8 \times 10^6$ | $<10^2$ |
| | 0.5 | $5.2 \times 10^6$ | $1.2 \times 10^3$ |
| No treatment | — | $5.8 \times 10^6$ | $5.8 \times 10^6$ |

The results of Tables 4 and 5 show that for the Examples, almost equal microbicidal effects were displayed by those immediately after preparation and those that were allowed to stand for 4 weeks. In contrast, the Comparative Examples were notably deactivated by heating treatment at 50° C. for 4 weeks. Specifically, it was found that the Examples are microbicidal liquid deodorants having excellent stability of active ingredients.

TEST EXAMPLE 3

Test of Fast-Acting Microbicidal Efficacy

*Escherichia* genus microbes, which were subjected to cell washing, were diluted with phosphate/citrate buffer solution (pH 8) to a concentration of approximately $10^6$ CFU/ml, and 1 L each of the prepared solution was poured into glass beakers. Example 1 or 8, and the powdered substance of Compound A1 were each added thereto so as to bring to a prescribed concentration (indicated based on active ingredient), respectively, and the mixtures were stirred for 90 minutes. A portion of each mixture was taken at 5, 10, 30, and 90 minutes and was diluted with sterilized water. Then, the diluted mixture was inoculated onto a nutrient plate agar medium and cultured in an incubator at 30° C. for 3 days. Then, viable cells therein were counted. The results are shown in Tables 6 and 7 in the unit of CFU/ml. Tables 6 and 7 indicate the results obtained by conducting the tests over two separate occasions under the above conditions.

TABLE 6

| | Conc. (ppm) | Contact time (min.) | | | |
|---|---|---|---|---|---|
| | | 5 | 10 | 30 | 90 |
| Example 1 | 2.0 | $<10^2$ | $<10^2$ | $<10^2$ | $<10^2$ |
| | 1.5 | $<10^2$ | $<10^2$ | $<10^2$ | $<10^2$ |
| | 1.0 | $<10^2$ | $<10^2$ | $<10^2$ | $<10^2$ |
| | 0.5 | $<10^2$ | $<10^2$ | $<10^2$ | $<10^2$ |
| | 0.25 | $3.0 \times 10^6$ | $3.1 \times 10^6$ | $4.3 \times 10^6$ | $2.7 \times 10^5$ |
| Powder of Compound A1 | 2.0 | $1.0 \times 10^5$ | $2.0 \times 10^4$ | $<10^2$ | $<10^2$ |
| | 1.5 | $3.3 \times 10^6$ | $5.0 \times 10^4$ | $2.0 \times 10^2$ | $<10^2$ |
| | 1.0 | $2.9 \times 10^6$ | $2.7 \times 10^5$ | $4.0 \times 10^3$ | $<10^2$ |
| | 0.5 | $3.0 \times 10^6$ | $7.7 \times 10^5$ | $8.0 \times 10^4$ | $<10^2$ |
| | 0.25 | $3.0 \times 10^6$ | $3.1 \times 10^6$ | $4.5 \times 10^5$ | $3.7 \times 10^5$ |
| No treatment | — | $4.0 \times 10^6$ | $3.7 \times 10^6$ | $5.0 \times 10^6$ | $1.1 \times 10^6$ |

TABLE 7

| | Conc. (ppm) | Contact time (min) | | | |
|---|---|---|---|---|---|
| | | 5 | 10 | 30 | 90 |
| Example 8 | 2.0 | $<10^2$ | $<10^2$ | $<10^2$ | $<10^2$ |
| | 1.5 | $<10^2$ | $<10^2$ | $<10^2$ | $<10^2$ |
| | 1.0 | $<10^2$ | $<10^2$ | $<10^2$ | $<10^2$ |
| | 0.5 | $<10^2$ | $<10^2$ | $<10^2$ | $<10^2$ |
| | 0.25 | $5.8 \times 10^6$ | $5.6 \times 10^6$ | $3.0 \times 10^6$ | $2.0 \times 10^5$ |
| Powder of compound A1 | 2.0 | $3.2 \times 10^5$ | $1.2 \times 10^4$ | $<10^2$ | $<10^2$ |
| | 1.5 | $4.3 \times 10^6$ | $3.0 \times 10^4$ | $<10^2$ | $<10^2$ |
| | 1.0 | $4.8 \times 10^6$ | $2.9 \times 10^5$ | $8.8 \times 10^3$ | $<10^2$ |
| | 0.5 | $5.0 \times 10^6$ | $6.7 \times 10^5$ | $8.0 \times 10^4$ | $<10^2$ |
| | 0.25 | $5.6 \times 10^6$ | $5.1 \times 10^6$ | $3.7 \times 10^5$ | $2.7 \times 10^5$ |
| No treatment | — | $6.0 \times 10^6$ | $5.8 \times 10^6$ | $5.1 \times 10^6$ | $5.1 \times 10^6$ |

The results of Tables 6 and 7 show that, compared with the solid compound, the Examples had enhanced solubility into the target object for killing of microbes, and clarify that the Examples exhibit excellent microbicidal effects within a very short period. This property is required for disinfection or slime control of water for paper manufacturing processes, cooling water and washing water for various industrial uses, and the like, which require quick microbicidal activity. These results show that the Examples are microbicidal liquid deodorants suitable for disinfection or slime control of water for paper manufacturing processes and the like, which require fast-acting microbicidal activity.

TEST EXAMPLE 4

Test of Sustainability of Deodorant Effect Against Active Sludge

Active sludge (dehydrated cake, water content 70%) obtained from a sewage treatment plant was used for tests on the deodorant effect. The obtained active sludge was suspended with distilled water to form a 40% suspension. Example 9, Comparative Example 2, or powdered Compound A2 was then added to the suspension in a prescribed amount (indicated based on active ingredient) and stirred. 200 g of each suspension containing Example 9, Comparative Example 2, or powdered Compound A2 was transferred to a 1-liter Erlenmeyer flask, and the flask was sealed with a rubber stopper provided with 2 glass pipes each having a rubber tube and a pinchcock. The volumes of ammonia, hydrogen sulfide, and methyl mercaptan which were generated in a gas phase part of the 1-liter Erlenmeyer flask were measured after 1 hour and after 7 days. The measurement of each gas component was conducted by inserting a gas detector tube into one of the rubber tubes with both pinchcocks open. Used herein were a gas detector 3L (GASTEC CORPORATION) for ammonia, a gas detector 3L (GASTEC CORPORATION) for hydrogen sulfide, and a gas detector 71 (GASTEC CORPORATION) for methyl mercaptan. The results are shown in Table 8. The symbol "ND" in the table indicates that a detected value was equal to or lower than the detection limit of the detector tube.

TABLE 8

|  | Conc. (ppm) | Volume of Ammonia (ppm) | | Volume of Hydrogen sulfide (ppm) | | Volume of Methyl mercaptan (ppm) | |
| --- | --- | --- | --- | --- | --- | --- | --- |
|  |  | 1 hour later | 2 hours later | 1 hour later | 2 hours later | 1 hour later | 2 hours later |
| Example 9 | 80 | ND | ND | ND | ND | ND | ND |
|  | 40 | ND | ND | ND | ND | ND | ND |
|  | 20 | 1 | ND | ND | ND | ND | ND |
|  | 10 | 10 | 10 | ND | ND | 0.5 | ND |
| Comparative Example 2 | 80 | ND | 5.0 | ND | ND | ND | 0.5 |
|  | 40 | ND | 20 | ND | 5.0 | ND | 5.0 |
|  | 20 | 5.0 | 40 | ND | 5.0 | ND | 10 |
|  | 10 | 20 | 40 | 2.5 | 5.0 | 5.0 | 10 |
| Powder of compound A2 | 80 | ND | 20 | ND | 5.0 | ND | 5.0 |
|  | 40 | 10 | 40 | 2.5 | 5.0 | 0.5 | 10 |
|  | 20 | 40 | 40 | 5.0 | 5.0 | 10 | 10 |
|  | 10 | 40 | 40 | 5.0 | 5.0 | 10 | 10 |
| No treatment | — | 40 | 40 | 5.0 | 5.0 | 10 | 10 |

The result of Table 8 shows that the Example exhibited an excellent deodorant effect within a short period, compared with the solid compound. This result indicates that the Example is a microbicidal liquid deodorant exhibiting an excellent deodorant effect within a short period. Further, even under a condition of weak stirring and insufficient mixing, because the Example was sufficiently dissolved and permeated into the target object, it exhibited a rapid deodorant effect with a smaller amount thereof.

What is claimed is:

1. A liquid microbicide comprising:
   one or more halogenated dialkyl hydantoin represented by formula (1):

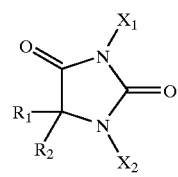

(1)

wherein $X_1$ and $X_2$ represent halogen atoms and $R_1$ and $R_2$ represent low alkyl groups, and a solvent comprising one or more thiophene derivative;
wherein one or more thiophene derivative is selected from the group consisting of tetrahydrothiophene 1,1-dioxide, 3-methyltetrahydrothiophene 1,1-dioxide, 2,5-dihydrothiophene 1,1-dioxide, and mixtures thereof.

2. The liquid microbicide according to claim 1, wherein one or more halogenated dialkyl hydantoin is selected from the group consisting of 1,3-dibromo-5,5-dimethylhydantoin, 1-bromo-3-chloro-5,5-dimethylhydantoin, 3-bromo-1-chloro-5,5-dimethylhydantoin, bromochloro-5,5-dimethylhydantoin, 1,3-dichloro-5,5-dimethylhydantoin, 1,3-dichloro-5-ethyl-5-methylhydantoin, and mixtures thereof.

3. The liquid microbicide according to claim 1, comprising one or more halogenated dialkyl hydantoin and tetrahydrothiophene 1,1-dioxide.

4. The liquid microbicide according to claim 1, further comprising one or more adjuvant; wherein one or more adjuvant is selected from the group consisting of hydantoin, 5,5-dimethylhydantoin, succinimide, phthalimide, and mixtures thereof.

5. The liquid microbicide according to claim 1, further comprising a known microbicide component.

6. The liquid microbicide according to claim 1, wherein one or more thiophene derivative is present in an amount of 100 or more parts by mass based on 100 parts by mass of halogenated dialkyl hydantoin.

7. The liquid microbicide according to claim 1, wherein one or more thiophene derivative is present in an amount of 200 to 900 parts by mass, based on 100 parts by mass of halogenated dialkyl hydantoin.

8. A method for killing microbes, which comprises:
   treating a target system or a target object for microbicidal treatment with an effective amount of an admixture comprising one or more halogenated dialkyl hydantoin represented by formula (1):

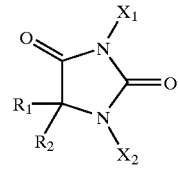

(1)

wherein $X_1$ and $X_2$ represent halogen atoms and $R_1$ and $R_2$ represent low alkyl groups, and/or
one or more halogenated succinimide represented by formula (2):

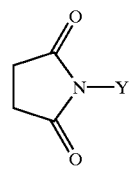

(2)

wherein Y represents a halogen atom; and
a solvent comprising one or more thiophene derivative;
wherein one or more thiophene derivative is selected from the group consisting of tetrahydrothiophene 1,1-dioxide, 3-methyltetrahydrothiophene 1,1-dioxide, 2,5-dihydrothiophene 1,1-dioxide and mixtures thereof.

9. A liquid deodorant comprising:
one or more halogenated dialkyl hydantoin represented by formula (1):

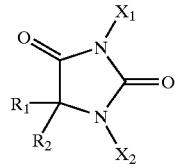
(1)

wherein $X_1$ and $X_2$ represent halogen atoms and $R_1$ and $R_2$ represent low alkyl groups, and
a solvent comprising one or more thiophene derivative;
wherein one or more thiophene derivative is selected from the group consisting of tetrahydrothiophene 1,1-dioxide, 3-methyltetrahydrothiophene 1,1-dioxide, 2,5-dihydrothiophene 1,1-dioxide; and mixtures thereof.

10. The liquid deodorant according to claim 9, wherein the halogenated dialkyl hydantoin is selected from the group consisting of 1,3-dibromo-5,5-dimethylhydantoin, 1-bromo-3-chloro-5,5-dimethylhydantoin, 3-bromo-1-chloro-5,5-dimethylhydantoin, bromochloro-5,5-dimethylhydantoin, 1,3-dichloro-5,5-dimethylhydantoin, 1,3-dichloro-5-ethyl-5-methylhydantoin, and mixtures thereof.

11. The liquid deodorant according to claim 9, comprising one or more halogenated dialkyl hydantoin and tetrahydrothiophene 1,1-dioxide.

12. The liquid deodorant according to claim 9, further comprising one or more adjuvant; wherein one or more adjuvant is selected from the group consisting of hydantoin, 5,5-dimethylhydantoin, succinimide, phthalimide, and mixtures thereof.

13. The liquid deodorant according to claim 9, further comprising a known microbicide component.

14. The liquid deodorant according to claim 9, wherein one or more thiophene derivative is present in an amount of 100 or more parts by mass based on 100 parts by mass of halogenated dialkyl hydantoin.

15. The liquid deodorant according to claim 9, wherein one or more thiophene derivative is present in an amount of 200 to 900 parts by mass, based on 100 parts by mass of halogenated dialkyl hydantoin.

16. A deodorizing method, which comprises:
treating a target system or a target object for deodorization with an effective amount of an admixture comprising one or more halogenated dialkyl hydantoin represented by formula (1):

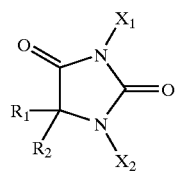
(1)

wherein $X_1$ and $X_2$ represent halogen atoms and $R_1$ and $R_2$ represent low alkyl groups, and/or
one or more halogenated succinimide represented by formula (2):

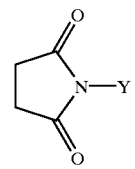
(2)

wherein Y represents a halogen atom; and
a solvent comprising one or more thiophene derivative;
wherein one or more thiophene derivative is selected from the group consisting of tetrahydrothiophene 1,1-dioxide, 3-methyltetrahydrothiophene 1,1-dioxide, 2,5-dihydrothiophene 1,1-dioxide and mixtures thereof.

17. A method for stabilizing a halogenated dialkyl hydantoin and/or halogenated succinimide, which comprises:
dissolving at least one substance selected from the group consisting of one or more halogenated dialkyl hydantoin represented by formula (1):

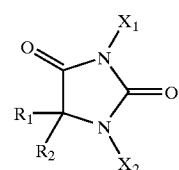
(1)

wherein $X_1$ and $X_2$ represent halogen atoms and $R_1$ and $R_2$ represent low alkyl groups, and/or
one or more halogenated succinimide represented by formula (2):

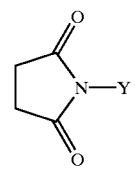
(2)

wherein Y represents a halogen atom;
in a solvent comprising one or more thiophene derivative;
wherein one or more thiophene derivative is selected from the group consisting of tetrahydrothiophene 1,1-dioxide, 3-methyltetrahydrothiophene 1,1-dioxide, 2,5-dihydrothiophene 1,1-dioxide and mixtures thereof.

18. A method for stabilizing a halogenated dialkyl hydantoin and/or halogenated succinimide according to claim 17, wherein at least one substance is selected from the group consisting of hydantoin, 5,5-dimethylhydantoin, succinimide, and phthalimide.

* * * * *